(12) United States Patent
Giron

(10) Patent No.: US 7,258,023 B2
(45) Date of Patent: Aug. 21, 2007

(54) PROCESS FOR MEASURING THE TRANSFER RESISTANCE OF A COSMETIC PRODUCT

(75) Inventor: Franck Giron, Ferrieres en Brie (FR)

(73) Assignee: L'Oreal S.A., Paris (FR)

( * ) Notice: Subject to any disclaimer, the term of this patent is extended or adjusted under 35 U.S.C. 154(b) by 442 days.

(21) Appl. No.: 11/007,180

(22) Filed: Dec. 9, 2004

(65) Prior Publication Data

US 2005/0183511 A1 Aug. 25, 2005

(30) Foreign Application Priority Data

Dec. 18, 2003 (FR) .................................. 03 51108

(51) Int. Cl.
*G01N 3/24* (2006.01)
*G01N 21/00* (2006.01)
(52) U.S. Cl. ......................................... 73/841; 436/164
(58) Field of Classification Search .................. 73/841; 436/164, 71; 424/64, 401
See application file for complete search history.

(56) References Cited

U.S. PATENT DOCUMENTS

| 6,254,876 | B1 * | 7/2001 | de la Poterie et al. | 424/401 |
| 6,340,466 | B1 * | 1/2002 | Drechsler et al. | 424/401 |
| 6,649,173 | B1 | 11/2003 | Arnaud et al. | |
| 6,958,155 | B2 * | 10/2005 | Lu et al. | 424/401 |
| 6,967,024 | B2 * | 11/2005 | Scancarella et al. | 424/401 |
| 2002/0128615 | A1 | 9/2002 | Tyrrell et al. | |
| 2003/0165429 | A1 | 9/2003 | Takeoka et al. | |
| 2005/0260762 | A1 * | 11/2005 | Giron | 436/164 |

FOREIGN PATENT DOCUMENTS

WO   WO 2004/055073 A2   7/2004

OTHER PUBLICATIONS

"Digital Ink Rub Tester," Internet Article, 'en lignel 2002, XP002291872.

* cited by examiner

*Primary Examiner*—Michael Cygan
*Assistant Examiner*—O. Davis
(74) *Attorney, Agent, or Firm*—Finnegan, Henderson, Farabow, Garrett & Dunner L.L.P.

(57) ABSTRACT

Disclosed herein is a process for measuring the transfer resistance of a cosmetic product, such as a foundation, comprising: i) depositing an amount of the cosmetic product onto a first face of a support; ii) applying the first face of the support onto a sheet, under given pressure and given duration conditions; iii) while maintaining a pressure, effecting a relative translational motion between the sheet and the support, parallel to the plane of the sheet and at a substantially constant speed; and iv) determining a transfer index for the product as a function of the amount of residual product on the first face, or in the event of a residual amount that is greater than zero and less than the said given amount, as a function of the length of a trail formed by the product transferred onto the sheet.

31 Claims, No Drawings

PROCESS FOR MEASURING THE TRANSFER RESISTANCE OF A COSMETIC PRODUCT

The present application claims benefit under 35 U.S.C. §119 to French application no. 03/51108, filed Dec. 18, 2003.

The present disclosure relates to the in vitro evaluation of the transfer resistance of a cosmetic product, for example a foundation.

To test the transfer resistance, or staying power, of a foundation, in vivo evaluations are usually performed.

The implementation of these in vivo tests may be constricting. Furthermore, certain permits must sometimes be obtained before applying any new composition in vivo, which may further complicate the implementation of the test.

There is thus a need for an in vitro test for evaluating the transfer resistance of a cosmetic product, which is capable of replacing the abovementioned in vivo tests.

U.S. Pat. No. 6,340,466 discloses an in vitro test for evaluating the transfer-resistance properties of a cosmetic product. This test uses, for example, a support consisting of a food-grade envelope to be rehydrated in a predetermined manner, onto which a film of the product is applied. After transfer by rotating and pressing the film on a support, the reflectance of the film transferred onto this support is measured. This test, which may be relatively complicated to implement, is not entirely satisfactory.

Thus, one of the objects of the present disclosure is to provide a method for performing an in vitro evaluation of the transfer resistance of a cosmetic product, such as a foundation, which may totally or partially solve the problems mentioned with the known methods.

Other embodiments will become apparent in the detailed description that follows.

According to the present disclosure, these embodiments may be achieved by performing a process for measuring the transfer resistance of a cosmetic product, such as a foundation, which comprises:

i) depositing a given amount of the cosmetic product onto a first face of a support, for example a support made of foam;
ii) applying the first face of the support onto a sheet, such as a sheet of paper, under pressure and duration conditions;
iii) while maintaining a pressure, effecting a relative translational motion between the sheet and the support, substantially in the plane of the sheet and at a substantially constant speed; and
iv) determining a transfer index for the cosmetic product:
   a. as a function of the amount of residual cosmetic product on the first face; or
   b. in the event of a non-zero residual amount that is greater than zero but less than the given amount of cosmetic product, as a function of the length of a trail formed by the cosmetic product transferred onto the sheet.

In certain embodiments, the sheet is displaced relative to the support, the support being fixed.

The amount of residual cosmetic product on the support may be assessed visually. Alternatively, weighings may be taken before and after the displacement.

As used herein, the term "non-zero residual amount" means an amount greater than 0% of the given amount, such as greater than 5% or greater than 10%.

In the case where the amount of residual product on the support is substantially zero, the transfer of the product may be termed "total".

Conversely, in the case where the amount of product transferred onto the sheet is substantially zero, i.e., in the case where the amount of residual product on the support is substantially equal to the given amount of product, the transfer may be termed "zero".

Between these two endpoint cases, the level of transfer of the cosmetic product is partial. The value of the transfer index is then directly related to the length of the trail of cosmetic product on the sheet.

Thus, the transfer index is within a range bounded by a first endpoint value attributed when the amount of residual product on the support is substantially zero, and by a second endpoint value attributed when the amount of residual product on the support is substantially equal to the given amount of cosmetic product.

Similarly, and according to one embodiment, the transfer index of the cosmetic product is equal to the first endpoint value when the amount of residual product is greater than zero, but substantially less than the given amount of cosmetic product and when the trail of cosmetic product extends over a length greater than a maximum length, such as beyond the edge of the sheet.

As a guide, the "grade" or "transfer index" may be on a scale ranging from 0 to 5.

According to one embodiment, the first face of the support is applied onto the sheet when the sheet is dry.

Alternatively, the first face of the support may be applied onto the sheet after a given amount of a liquid, for example a liquid chosen from at least one of sebum, sweat, and water, has been applied onto the sheet. The nature of the liquid may be chosen as a function of the normal conditions of use of the product and may correspond to one or more liquids with which the cosmetic product is liable to come into contact during its use.

It is understood that the products, as a function of their nature, may be tested either in dry form, in the presence of at least one liquid, or successively in the presence of more than one liquid.

A second face of the support, opposite the first, may be coated with an adhesive surface. This adhesive surface may allow the support to be attached to a tool for applying the given pressure.

The given pressure may be applied by means of a tensile testing press.

The given pressure may range from 200 $g/cm^2$ to 2 $kg/cm^2$, such as from 100 $g/cm^2$ to 2 $kg/cm^2$.

The given duration may be range from 1 second to 20 seconds, such as from 2 seconds to 10 seconds.

In certain embodiments, the sheet is a sheet of photo-quality paper.

The support may be made of foam, for example, it may be made of neoprene.

In certain embodiments, the sheet is displaced at a speed ranging from 1 cm/s to 15 cm/s, such as from 2 cm/s to 10 cm/s.

The cosmetic product may be deposited onto the first face by:

i) bonding a crown of a given thickness to the first face;
ii) depositing the cosmetic product inside the crown;
iii) leveling off the cosmetic product thus deposited such that its thickness is substantially identical to that of the crown;
iv) leaving the cosmetic product to dry; and
v) removing the crown.

In certain embodiments, the crown is made of a sheet material with a thickness ranging from 50 μm to 400 μm, such as from 150 μm to 300 μm.

When the cosmetic product is colored, the length of the trail may be determined visually. Alternatively, the measurement may be automated by means of a calorimetric measurement, for example using a camera.

The cross section of the volume defined inside the crown can be of any shape, such as circular, triangular, rectangular, or square.

When the cosmetic product is uncolored, the process may further comprise a revelation step so as to make the product visible on the sheet. Such an uncolored product may be, for example, a skincare product or a product for protecting against the harmful effects of sunlight.

The revelation step may comprise incorporating into the product a compound capable of re-emitting in the visible range all or some of a radiation to which the compound is exposed, for example UV radiation. By way of example, the radiation emitted by a Wood lamp may be used.

In certain embodiments, the sheet is subdivided into a plurality of areas, which are successively displaced under the support during the translational displacement of the sheet, the number of areas over all or some of which the trail of cosmetic product extends being representative of the staying power of the cosmetic product. As a guide, the number of areas may range from 2 to 10, such as from 4 to 7.

In certain embodiments, the cosmetic product is chosen from foundations, makeup rouges, eyeshadows, and blushers.

One embodiment disclosed herein is a method for promoting a cosmetic product, comprising quoting a transfer resistance as measured by the process disclosed herein.

Such a promotion of the cosmetic product may be performed via any channel of communication. It may be performed, for example, by the vendor, directly at the point of sale, and/or via radio and television, for example in the context of advertisements. It may also be performed via the published press and/or by means of any other document, such as documents for advertising purposes (e.g., leaflets). It may also be performed via the Internet and/or via any other suitable computer network. It may also be performed directly on the cosmetic product, for example on its packaging and/or on any explanatory notice that may be associated therewith.

Visual material may be associated with such a promotion, for example in the form of photographs, videos, and any other form of illustration, such as graphic forms.

Besides the embodiments outlined above, disclosed herein are other embodiments that will be explained below, with regard to a non-limiting implementation example, described in detailed manner in the section that follows.

Other than in the implementation example, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the invention are approximations, unless otherwise indicated the numerical values set forth in the specific example is reported as precisely as possible. Any numerical value, however, inherently contain certain errors necessarily resulting from the standard deviation found in their respective testing measurements. The following example is intended to illustrate the invention without limiting the scope as a result.

EXAMPLE

A support (square of 40 mm×40 mm) comprising a layer of neoprene foam that is adhesive on one of its faces (sold under the name RE70X40 212B from the company Joint Technique Lyonnais Ind) was prepared.

An adhesive crown having an inside diameter of 24 mm and a thickness of about 250 μm was fixed onto the non-adhesive face of the support. The composition was applied inside the crown and was leveled off with a glass slide to obtain a deposit of composition about 250 μm thick. The crown was then removed and the deposit was left to dry for 20 hours in an oven at 37° C.

The support was then bonded via its adhesive face to a tip 27 mm in diameter attached to a press (Statif Manuel SV-1 from the company Imada Co. Ltd.) equipped with a tensile testing machine (DPS-5R from the company Imada Co. Ltd.).

A strip 4 cm wide and 21 cm long was drawn on a photo-quality coated paper (reference Epson S041061 with a basis weight of 102 $g/m^2$) and 5 boxes each 4.2 cm long were drawn inside this strip in the longitudinal axis of the strip. The paper was placed on the bed of the press.

A drop of 10 μl of artificial sebum having the following composition:

| | |
|---|---|
| triolein | 29% |
| oleic acid | 28.5% |
| oleyl oleate | 18.5% |
| squalene | 14% |
| cholesterol | 7% |
| cholesteryl palmitate | 3% | was placed in the center of the first box.

The support (comprising a sample of composition) was then pressed onto the first box of the strip of paper, with a force of about 4 kg exerted for 5 seconds. The paper was then displaced in a straight and uniform manner over the entire length of the strip such that the support came into contact with the entire length of the strip. The displacement speed of the strip was about 10 cm/s.

The trail of product deposited on the strip of paper was then observed visually. A grade ranging from 0 to 5 in increments of 0.5 was attributed as a function of the number of boxes, from the first to the fifth, possibly totally or partially crossed by the trail of product.

The grade 5 was attributed when, by observation, after the relative displacement between the paper and the support has been performed, there was substantially no product remaining on the support. In this case, the transfer may be termed "total".

The grade 5 was also attributed when the trail of product extended beyond the fifth box, independently of the amount of product remaining on the support.

The grade 0 was attributed when no product present on the support was transferred into the strip of paper, i.e., no visible trace was observed on the sheet. In this case, the transfer may be termed zero.

Conventionally, the separating line between box n and box n+1 forms part of box n.

The table below illustrates the way in which the other grades were attributed as a function of the place on the boxes 1 to 5 at which the trail of product stopped. For these grades, a larger or smaller amount of product remained on the support, i.e., the transfer was partial.

|  | Grade | |
| --- | --- | --- |
| Number of the box at which the trail of product stops | More than half of the box | Up to half of the box |
| 5 | 4.5 | 4 |
| 4 | 3.5 | 3 |
| 3 | 2.5 | 2 |
| 2 | 1.5 | 1 |
| 1 | 0.5 | |

In the preceding detailed description, reference has been made to preferred embodiments. Variants may be made thereto without departing from the spirit of the disclosure.

What is claimed is:

1. A process for measuring the transfer resistance of a cosmetic product comprising:
    i) depositing an amount of the cosmetic product onto a first face of a support;
    ii) applying the first face of the support onto a sheet, under pressure and duration conditions;
    iii) while maintaining a pressure, effecting a relative translational motion between the sheet and the support, parallel to the plane of the sheet and at a substantially constant speed; and
    iv) determining a transfer index for the cosmetic product:
        a. as a function of the amount of residual product on the first face; or
        b. if the residual amount is greater than zero and less than the amount deposited in step i), as a function of the length of a trail formed by the cosmetic product transferred onto the sheet.

2. The process according to claim 1, wherein the cosmetic product is a foundation.

3. The process according to claim 1, wherein the support is made of foam.

4. The process according to claim 1. wherein the sheet is paper.

5. The process according to claim 1, wherein the first face of the support is applied onto the sheet when the sheet is dry.

6. The process according to claim 1, wherein the first face of the support is applied onto the sheet after an amount of a liquid has been applied onto the sheet.

7. The process according to claim 6, wherein the liquid is chosen from at least one of sebum, sweat, and water.

8. The process according to claim 1, wherein a second face of the support, opposite the first face, is coated with an adhesive surface.

9. The process according to claim 1, wherein the pressure is applied by means of a tensile testing press.

10. The process according to claim 1, wherein the pressure ranges from 200 g/cm$^2$ to 2 kg/cm$^2$.

11. The process according to claim 10, wherein the pressure ranges from 100 g/cm$^2$ to $^2$ kg/cm$^2$.

12. The process according to claim 1, wherein the duration ranges from 1 second to 20 seconds.

13. The process according to claim 12, wherein the duration ranges from 2 seconds to 10 seconds.

14. The process according to claim 1, wherein the sheet is a sheet of photo-quality paper.

15. The process according to claim 3, wherein the foam is neoprene.

16. The process according to claim 1, wherein the sheet is displaced at a speed ranging from 1 cm/s to 15 cm/s.

17. The process according to claim 16, wherein the sheet is displaced at a speed ranging from 2 cm/s to 10 cm/s.

18. The process according to claim 1, comprising depositing the cosmetic product onto the first face by:
    i) bonding a crown to the first face;
    ii) depositing the cosmetic product inside the crown;
    iii) leveling off the cosmetic product thus deposited such that the thickness of the cosmetic product is substantially identical to that of the crown;
    iv) leaving the cosmetic product to dry; and
    v) removing the crown.

19. The process according to claim 18, wherein the crown is made of a sheet material with a thickness ranging from 50 μm to 400 μm.

20. The process according to claim 19, wherein the crown has a thickness ranging from 150 μm to 300 μm.

21. The process according to claim 1, wherein the cosmetic product is colored.

22. The process according to claim 21, wherein the length of the trail is determined visually.

23. The process according to claim 1, wherein the cosmetic product is uncolored.

24. The process according to claim 23, further comprising revealing the cosmetic product so as to make it visible on the sheet.

25. The process according to claim 24, comprising incorporating into the product a compound capable of re-emitting in the visible range at least some of a radiation to which the compound is exposed.

26. The process according to claim 25, wherein the radiation is UV radiation.

27. The process according to claim 1, wherein the sheet is subdivided into at least two areas, which areas are successively displaced under the support during the translational displacement of the sheet, and further wherein the number of areas over at least some of which the trail of cosmetic product extends represents the transfer resistance of the cosmetic product.

28. The process according to claim 1, wherein the transfer index is within a range bounded by a first value attributed when the amount of residual product on the support is substantially zero, and by a second value attributed when the amount of residual product on the support is substantially equal to the amount of product deposited.

29. The process according to claim 28, wherein the transfer index is equal to the first value when the amount of residual product is greater than zero but less than the amount of product deposited and when the trail of product extends over a length greater than a maximum length.

30. The process according to claim 1, wherein the cosmetic product is chosen from foundations, makeup rouges, eyeshadows, and blushers.

31. A method for promoting a cosmetic product, comprising making reference to transfer resistance of the cosmetic product, wherein the transfer resistance is measured by a process comprising:

v) depositing an amount of the cosmetic product onto a first face of a support;

vi) applying the first face of the support onto a sheet, under pressure and duration conditions;

vii) while maintaining a pressure, effecting a relative translational motion between the sheet and the support, parallel to the plane of the sheet and at a substantially constant speed; and viii) determining a transfer index for the cosmetic product:

a. as a function of the amount of residual product on the first face; or b. in the event of a residual amount that is greater than zero and less than the amount deposited in step i), as a function of the length of a trail formed by the cosmetic product transferred onto the sheet.

* * * * *

UNITED STATES PATENT AND TRADEMARK OFFICE
CERTIFICATE OF CORRECTION

PATENT NO. : 7,258,023 B2
APPLICATION NO. : 11/007180
DATED : August 21, 2007
INVENTOR(S) : Franck Giron It is certified that error appears in the above-identified patent and that said Letters Patent is hereby corrected as shown below:

In claim 11, column 5, line 67, "$^2$kg/cm$^2$." should read --2 kg/cm$^2$.--

Signed and Sealed this

Twentieth Day of November, 2007

JON W. DUDAS
*Director of the United States Patent and Trademark Office*